US00PP19349P3

(12) United States Plant Patent
Danziger

(10) Patent No.: US PP19,349 P3
(45) Date of Patent: Oct. 21, 2008

(54) ***SUTERA* PLANT NAMED 'DANCOP21'**

(50) Latin Name: *Sutera cordata*
Varietal Denomination: DANCOP21

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/717,379

(22) Filed: Mar. 14, 2007

(65) Prior Publication Data

US 2008/0229464 P1 Sep. 18, 2008

(51) Int. Cl.
*A01H 5/00* (2006.01)

(52) U.S. Cl. ..... Plt./485; Plt./263

(58) Field of Classification Search ..... Plt./485, Plt./263

See application file for complete search history.

*Primary Examiner*—Annette H Para
*Assistant Examiner*—S. B. McCormick-Ewoldt
(74) *Attorney, Agent, or Firm*—Foley & Lardner LLP

(57) ABSTRACT

A new and distinct *Sutera* plant named 'DANCOP21' particularly characterized by 5-petalled flowers, measuring about 1.9 cm in diameter and purple in color with a yellow-orange colored throat; trailing, compact growth habit; early flowering response; and suitable for use with hanging basket planters, combination planters and ground cover under full sunlight-and slight shade.

2 Drawing Sheets

Latin name of the genus and species of the claimed plant: *Sutera cordata.*
Variety denomination: 'DANCOP21'.

BACKGROUND OF THE INVENTION

The present invention relates to a new and distinct cultivar of *Sutera* plant, botanically known as *Sutera cordata,* hereinafter referred to by the cultivar name 'DANCOP21'.

*Sutera,* of the Scrophulariaceae family, consists of annuals, which are grown in most climate zones in the U.S., and only in zones 9 and 10 if it is a perennial plant.

The new *Sutera* cultivar is a product of a planned breeding program conducted by the inventor, Gabriel Danziger, in Moshav Mishmar Hashiva, Israel. The objective of the breeding program is to develop a new *Sutera* variety with large, purple flowers and a trailing, compact growth habit.

The new *Sutera* cultivar originated from open pollination in a controlled breeding program by the inventor in 2005, in Moshav Mishmar Hashiva, Israel. Open pollination of the seed parent, an unpatented *Sutera* cultivar designated 'CV-04-72', by an unknown *Sutera* cultivar, took place in the controlled breeding program in Moshav Mishmar Hashiva, Israel. The new *Sutera* 'DANCOP21' was discovered and selected by the inventor, Gabriel Danziger, as a single flowering plant within the progeny of the stated cross in a controlled environment in Moshav Mishmar Hashiva, Israel.

Asexual reproduction of the new *Sutera* cultivar by vegetative tip cuttings was first performed in May of 2005 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DANCOP21', which in combination distinguish this *Sutera* as a new and distinct cultivar:

1. 5-petalled flowers, measuring about 1.9 cm in diameter and purple in color with a yellow-orange colored throat;
2. Trailing, compact growth habit;
3. Early flowering response; and
4. Suitable for use with hanging basket planters, combination planters and ground cover under full sunlight-and slight shade.

Plants of the new *Sutera* 'DANCOP21' differ from plants of the parental cultivar, 'CV-04-72' (unpatented) in the characteristics described in Table 1.

TABLE 1

| Characteristic | New Cultivar 'DANCOP21' | Female Parent 'CV-04-72' (unpatented) |
|---|---|---|
| Flower size | Large, about 1.9 cm | Medium, about 1.3 cm |
| Flower color | Purple | Light Blue |
| Leaf size (width) | Medium, about 1.6 cm | Small, about 1.0 cm |

Of the many commercial cultivars known to the present inventor, the most similar in comparison to the new *Sutera* 'DANCOP21' is the *Sutera* 'DANGUL14' (patented, U.S. Plant Pat. No. 18,194), in the characteristics described in Table 2:

TABLE 2

| Characteristic | New Cultivar 'DANCOP21' | Comparison Cultivar 'DANGUL14' (Patented, U.S. Plant Pat. No. 18,194) |
|---|---|---|
| Flower size | Large, about 1.9 cm | Extra large, about 2.7 cm |
| Flower color | Purple | White |
| Leaf size (width) | Medium, about 1.6 cm | Large, about 2.0 cm |

BRIEF DESCRIPTION OF THE DRAWINGS

The accompanying photographic drawings illustrate the overall appearance of the new *Sutera* 'DANCOP21' showing the colors as true as is reasonably possible with colored reproductions of this type. Colors in the photographs may differ slightly from the color value cited in the detailed botanical description, which accurately describe the color of 'DANCOP21'.

DETAILED BOTANICAL DESCRIPTION

Figure 1:
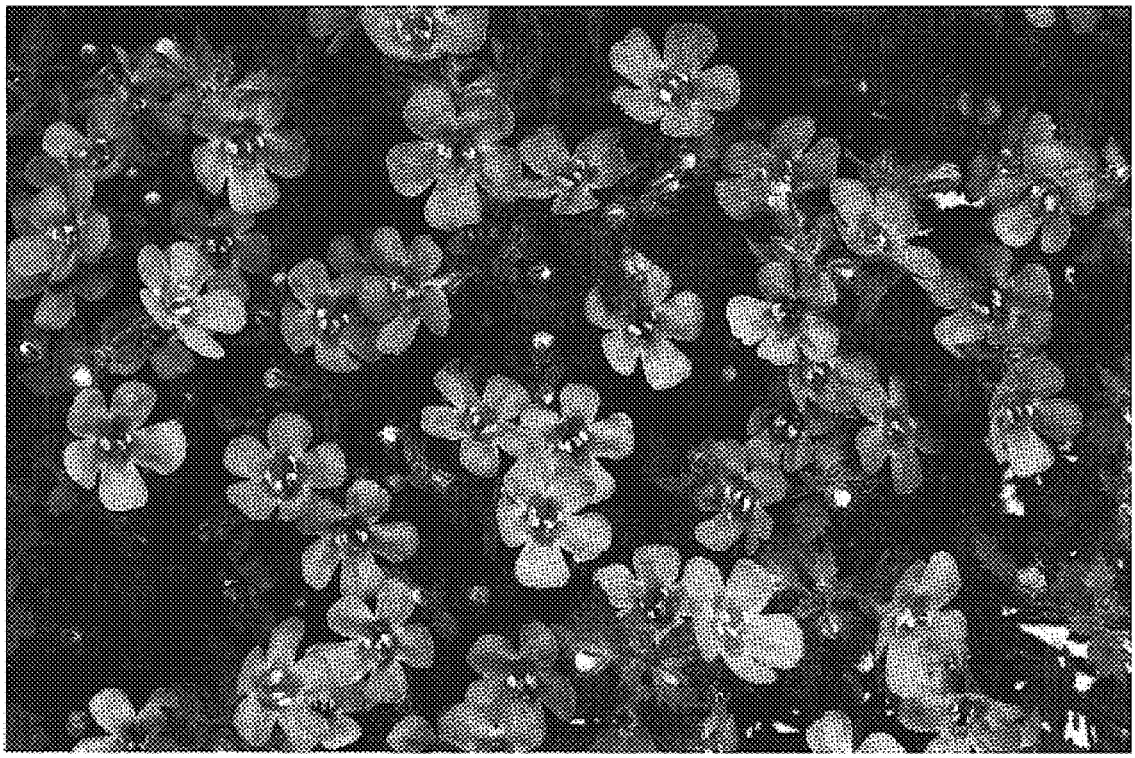
FIG. 1 shows a side view perspective of a typical flowering plant of 'DANCOP21' in a hanging planter at 3 months of age.
Figure 2:
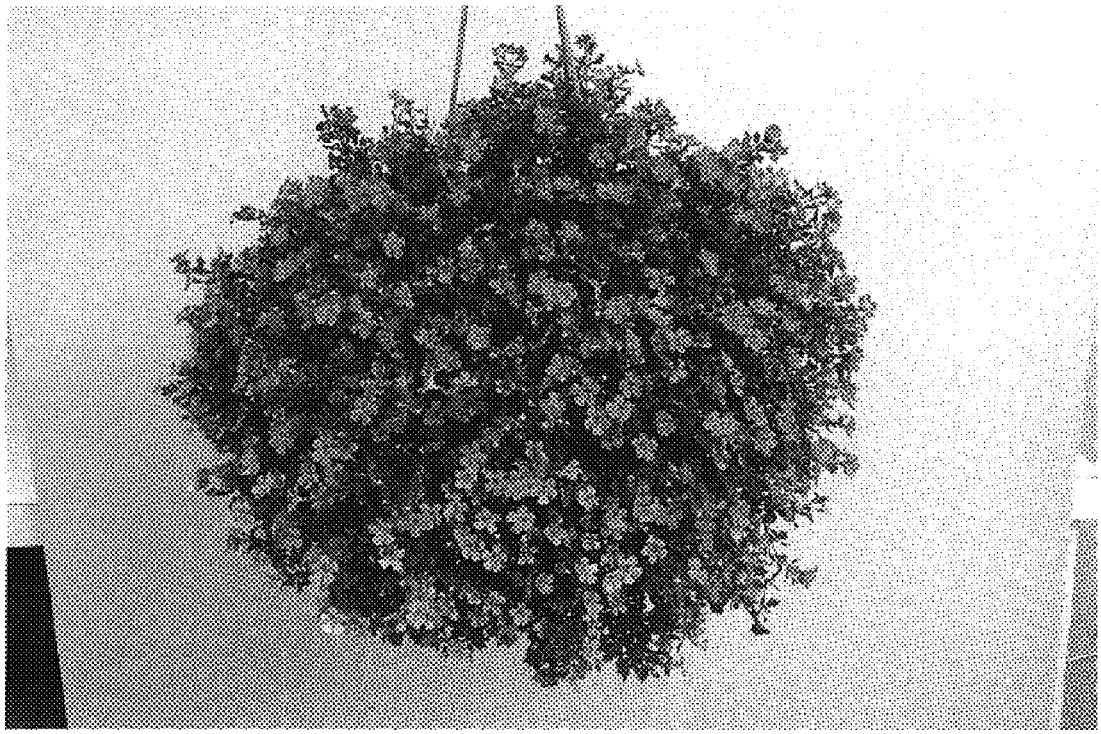
FIG. 2 shows a close-up view of typical flowers and buds of 'DANCOP21' at 3 months of age.

The new *Sutera* 'DANCOP21' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sutera* 'DANCOP21' as grown in a greenhouse in Moshav Mishmar Hashiva, Israel, under conditions which closely approximate those generally used in commercial practice.

Color references are made to The Royal Horticultural Society Colour Chart (R.H.S.), 2001 edition, except where general colors of ordinary significance are used. Color values were taken under daylight conditions at approximately 12:00 noon in Moshav Mishmar Hashiva, Israel. The age of the plant described is 3 months.

Classification:

*Botanical.*—*Sutera cordata.*

*Commercial.*—*Bacopa* Scopia™ Great Purple.

Parentage:

*Female or seed parent.*—*Sutera* cultivar designated 'CV-04-72' (unpatented).

*Male or pollen parent.*—Open pollination, unknown *Sutera* cultivar.

Optimal growth conditions:

*Light intensities.*—Full sunlight or slight shade.

*Temperature.*—Day: 20° C. to 24° C. Night: 16° C. to 20° C.

*Temperature tolerance.*—Tolerant to a low temperature of about 10° C. and tolerant to a high temperature of about 30° C.

*Fertilization.*—A balanced fertilizer with level of 100 ppm Nitrogen.

*Growth regulators.*—Unnecessary.

Propagation:

*Type.*—Tip cuttings of side shoots.

*Rooting habit and description.*—Easy to root; fine, fibrous roots.

*Time to initiate roots.*—About 7 to 10 days at 18° C.

*Time to produce a rooted cutting.*—About 14 days at 18°° C.

Plant:

*General appearance and form.*—Height: About 15 cm. Spread: About 50 cm.

*Shape.*—Trailing, vigorous growth habit.

*Winter hardiness.*—Hardy in moderate climate.

*Vigor.*—Strong.

*Crop time.*—About 8 to 10 weeks for a flowering pot.

*Fragrance.*—None.

*Branching habit.*—Vigorously branched. Lateral branches:

TABLE 3

| Branch characteristic | Primary | Secondary |
|---|---|---|
| Length | About 50 cm. | About 30 cm. |
| Diameter | About 2 mm. | About 1 mm. |
| Internode Length | About 2 cm. | About 1 cm. |
| Texture | Slightly rough | Slightly rough |
| Pubescence | Present | Present |
| Color | Yellow-Green, RHS 146B | Yellow-Green, RHS 146B |

Foliage:

*Arrangement and attachment.*—Opposite, petiolate.

*Leaf length.*—About 2.3 cm.

*Leaf width.*—About 1.5 cm.

*Overall shape of leaf.*—Ovate.

*Apex shape.*—Acute.

*Base shape.*—Acuminte.

*Margin.*—Dentate.

*Texture* (*both surfaces*).—Slightly velvety.

*Pubescence* (*both surfaces*).—Slightly present.

*Color of upper surface.*—Mature leaf: Green, RHS 137A. Immature leaf: Green, RHS 137B.

*Color of lower surface.*—Mature leaf: Green, RHS 137C. Immature leaf: Green, RHS 137C.

*Venation.*—Pattern: Palmate. Color: Upper surface: Green, RHS 137A. Lower surface: Green, RHS 137C.

*Petiole.*—Length: About 5 mm. Diameter: 1 mm. Color: Green, RHS 137A.

*Leaf fragrance.*—None.

Flower description:

*Natural flowering season.*—All year round in moderate climate. Flowering occurs between January and December outdoors in Israel.

*Flowering response time.*—About 4 weeks from planting.

*Flowering longevity.*—On the plant: Flowering of a single flower lasts for 7 days.

*Flower fragrance.*—None.

*Quantity of flowers and buds per plant.*—Approximately 200.

*Flower bud* (*about 2 days prior to opening*).—Shape: Spatulate. Length: About 10 mm. Diameter: About 5 mm. Texture: Velvety. Color: Violet, RHS N88A.

*Flower type.*—Solitary, auxillary.

*Flower form.*—Salverform.

*Flower symmetry.*—Radial symmetric.

*Orientation at opening.*—Slanted upward and outward.

*Corolla size.*—Diameter (spread): About 1.9 cm. Diameter at lobes: About 19 mm. Overall flower height: About 11 mm. Length of corolla tube: About 9 mm. Diameter of corolla tube: About 3 mm.

*Petals.*—Quantity: 5. Length: About 7 mm. Width: About 6 mm. Overall shape: Rounded and gameopetalous. Apex: Rounded. Base: Fused. Margin: Entire. Texture (upper & lower surfaces): Slightly velvety. Color: Upper surface, when opening: Purple, RHS N87A of violet group. Lower surface, when opening: Purple, RHS N87B of violet group. Upper surface, when opened: Purple, RHS N87B of violet group. Lower surface, when opened: Purple, RHS N87C of violet group. Corolla throat color: Yellow-orange, RHS 17A.

Calyx:

*Sepals.*—Quantity: 5. Length: About 5.0 mm. Width: About 1.0 mm. Overall shape: Linear. Apex: Acute. Base: Fused. Margin: Entire. Texture: Upper surface: Velvety. Lower surface: Velvety. Upper surface color: Green, RHS 137B. Lower surface color: Green, RHS 137B. Anthocyanin pigmentation of calyx limb: Absent.

*Pedicel.*—Aspect: Slanted upward. Length: About 7 mm. Diameter: About 1.0 mm. Angle: About 45°. Texture: Velvety. Color: Green, RHS 137C.

Reproductive organs:

*Androecium.*—Stamen: Number: 4. Arrangement: Didynamous. Type: Basifixed. Dehiscence of stamens: Extrorse. Color: Yellow, RHS 13A. Anthers: Shape: Cylinder. Length: About 1.0 mm. Color: Yellow, RHS 13B. Filaments: Length: About 10 mm. Color: Green-Yellow, RHS 1C. Pollen: Amount: Moderate. Color: Yellow, RHS 13C. Pollination requirements: Young flowers, active pollen, and receptive, open stigma.

*Gynoecium.*—Pistils: Quantity: 1. Length: About 10 mm. Stigma: Shape: Undulate. Width: About 0.5 mm. Color: Yellow-Green, RHS 150B. Style: Shape: Terete. Length: About 10 mm. Ovary: Shape: Ellipsoid. Position: Superior. Length: About 2.0 mm. Width: About 1.0 mm. Color: Green, RHS 143C.

Seeds:

*Quantity per fruit.*—About 20.

*Shape.*—Rounded.

*Length.*—About 0.5 mm.

*Width.*—About 0.5 mm.

*Texture.*—Rough.

*Color.*—Greyed-Orange, RHS 165C.

Fruit:

*Type.*—Capsule.

*Shape.*—Ellipsoid.

*Length.*—About 3.0 mm.

*Width.*—About 1 mm.

*Texture.*—Rugose.

*Color.*—Greyed-Orange, RHS 165B.

Disease/pest resistance: No information is currently available.

Disease/pest susceptibility: No information is currently available.

I claim:

1. A new and distinct *Sutera* plant named 'DANCOP21', as illustrated and described herein.

* * * * *